(12) United States Patent
Bunce

(10) Patent No.: US 8,802,434 B2
(45) Date of Patent: Aug. 12, 2014

(54) BIOLOGICAL CELL CULTURE, CELL CULTURE MEDIA AND THERAPEUTIC USE OF BIOLOGICAL CELLS

(75) Inventor: Christopher Martin Bunce, Birmingham (GB)

(73) Assignee: The University of Birmingham (GB)

( * ) Notice: Subject to any disclaimer, the term of this patent is extended or adjusted under 35 U.S.C. 154(b) by 836 days.

(21) Appl. No.: 10/581,376

(22) PCT Filed: Nov. 16, 2004

(86) PCT No.: PCT/GB2004/004826
§ 371 (c)(1),
(2), (4) Date: Jan. 31, 2007

(87) PCT Pub. No.: WO2005/056780
PCT Pub. Date: Jun. 23, 2005

(65) Prior Publication Data
US 2007/0243171 A1     Oct. 18, 2007

(30) Foreign Application Priority Data
Dec. 5, 2003 (GB) .................... 0328245.6

(51) Int. Cl.
*A61K 38/20* (2006.01)
*C12N 5/00* (2006.01)
*C12N 5/0775* (2010.01)
*C07K 14/52* (2006.01)
*C07K 14/54* (2006.01)
*C12N 5/071* (2010.01)

(52) U.S. Cl.
USPC ......... 435/386; 424/93.7; 424/93.1; 435/377; 435/325; 435/383; 435/384; 435/374; 514/7.6; 514/615

(58) Field of Classification Search
None
See application file for complete search history.

(56) References Cited

U.S. PATENT DOCUMENTS
5,834,217 A * 11/1998 Levine et al. ................ 435/7.24

FOREIGN PATENT DOCUMENTS
EP        1697503 B1    10/2011
WO    WO 03074074 A1 *  9/2003

OTHER PUBLICATIONS

Okabe-Kado Junko et al., "Physiological and pathological relevance of extracellular NM23/NDP kinases," Journal of Bioenergetics and Biomembranes, XP008031558, vol. 35 ( No. 1), p. 89-93, (Feb. 6, 2003).

Okabe-Kado Junko et al., "Inhibitory action of nm23 proteins on induction of erythroid differentiation of human leukemia cells," Biochimica Et Biophysica Acta, XP008031891, vol. 1267 ( No. 2-3), p. 101-106, (1995).

(Continued)

*Primary Examiner* — Jon P Weber
*Assistant Examiner* — Aaron J Kosar
(74) *Attorney, Agent, or Firm* — Berliner & Associates

(57) ABSTRACT

The protein NM23 is disclosed as an agent for the maintenance of undifferentiated biological cells in culture. The NM23 protein may act as a survival factor for such cultured cells, or to prevent the differentiation and maturation of the cultured cells. The use of NM23 protein is applicable to culture of stem and/or progenitor cells, and particularly to such cells cultured and adapted for therapeutic use. The invention provides methods, media and media supplements for use in the culture of biological cells, and further provides methods of preparing biological cells for therapeutic use, as well as methods of therapy utilising biological cells and medicaments comprising biological cells adapted for therapeutic use.

12 Claims, 9 Drawing Sheets

(56) References Cited

OTHER PUBLICATIONS

Figure 2:
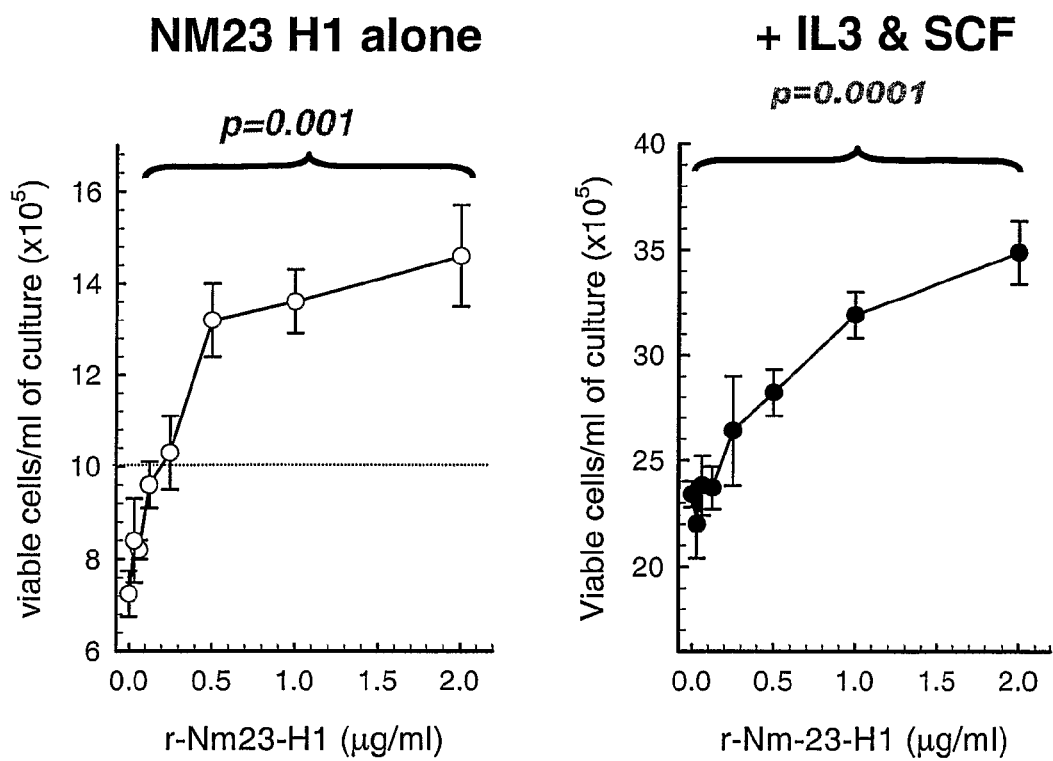

Okabe-Kado J et al., "Identity of a differentiation inhibiting factor for mouse myeloid leukemia cells with NM23/nucleoside diphosphate kinase," XP008031856, Biochemical and Biophysical Research Communications, vol. 182 ( No. 3), p. 987-994, (Feb. 14, 1992).

Lombardi Daniela et al., "nm23: Unraveling its biological function in cell differentiation," Journal of Cellular Physiology, XP008031851, vol. 182 ( No. 2), p. 144-149, (Feb. 6, 2000).

Negroni A et al., "Neuroblastoma specific effects of DR-nm23 and its mutant forms on differentiation and apoptosis," Cell Deatha nd Differentiation, XP008031853, vol. 7 ( No. 9), p. 843-850, (Sep. 6, 2000).

Willems Roel et al, "Decrease in nucleoside diphosphate kinase (NDPK/nm 23) expression during hematopoietic maturation," Journal of Biological Chemistry, XP002285299, vol. 273 ( No. 22), p. 13663-1366, (May 29, 1998).

Venturelli D et al., "Overexpression of DR-NM23, a protein encoded by a member of the NM23 Gene Family, inhibits Granulocyte Differentiation and Induces Apoptosis in 32DC13 Myeloid Cells," Proceedings of the National Academy of Sciences of USA, National Academy of Science, XP002942044, p. 7435-7439, (Aug. 6, 1995).

Gervasi Fabio et al., "Nm23 Influences proliferation and differentiation of PC12 cells ," Cell Growth and Differentiation, XP008031890, vol. 7 ( No. 12), p. 1689-1695, (Dec. 1996).

"Extracellular nucleoside diphosphate kinase NM23/NDPK modulates normal hematopoietic differentiation", Roel Willems et al., Experimental Hematology 30 (2002) pp. 640-648.

"Effect of Hematopoietic Growth Factors on Short Expansion of Umbilical Cord Blood CD34+ Cells in vitro" by Ye Yun-bin et al., Journal Fujian Medical University, vol. 37, No. 2, p. 147-150, (2003).

"Transplant fo marrow stem cell on ischemic heart disease" by Shan Shou-Jie et al, Chin J Clin Pharmacol Ther, Oct. 7, 2002(5), p. 473-476.

Jul. 5, 2012 Opposition filed in related European Patent 1697503, 17 pages.

Declaration of Cynthia Bamdad referred to in Jul. 5, 2012 Opposition at p. 31, item 6.2.9., 39 pages.

Dec. 20, 2013 further reply from opposer to patentee's comments, 33 pages.

Images submitted with and referred to in the Dec. 20, 2013 reply, 9 pages.

Miyamoto, T., et al., AML1/ETO-expressing nonleukemic stem cells in acute myelogenous leukemia with 8;21 chromosomal translocation, Proc. Natl. Acad. Sci. USA (2000) 97(13):7521-6, 6 pages.

Smagghe,B.J., et al., MUC1* ligand, NM23-H1, is a novel growth factor that maintains human stem cells in a more naive state, PLSO One (2113) 8(3): e58601, 15 pages.

* cited by examiner 1    mancertfia ikpdgvqrgl vgeiikrfeq kgfrlvglkf mqasedllke hyvdlkdrpf
61   faglvkymhs gpvvamvweg lnvvktgrvm lgetnpadsk pgtirgdfci qvgrniihgs
121  dsvesaekei glwfhpeelv dytscaqnwi ye

SEQUENCE ID NO. 1

1    atggccaact gtgagcgtac cttcattgcg atcaaaccag atggggtcca gcggggtctt
61   gtgggagaga ttatcaagcg ttttgagcag aaaggattcc gccttgttgg tctgaaattc
121  atgcaagctt ccgaagatct ctcaaggaa cactacgttg acctgaagga ccgtccattc
181  tttgccggcc tggtgaaata catgcactca gggccggtag ttgccatggt ctgggagggg
241  ctgaatgtgg tgaagacggg ccgagtcatg ctcggggaga ccaaccctgc agactccaag
301  cctgggacca tccgtggaga cttctgcata caagttggca ggaacattat acatggcagt
361  gattctgtgg agagtgcaga gaaggagatc ggcttgtggt ttcaccctga ggaactggta
421  gattacacga gctgtgctca gaactggatc tatgaatga

SEQUENCE ID NO. 2

Figure 1

BIOLOGICAL CELL CULTURE, CELL CULTURE MEDIA AND THERAPEUTIC USE OF BIOLOGICAL CELLS

REFERENCE TO SEQUENCE LISTING

Included with this application is a compact disc containing the sequence listing appended at the end of the specification.

The present invention relates to a method of preparing biological cells for therapeutic use, as well as to methods of therapy utilising biological cells, and to medicaments comprising biological cells adapted for therapeutic use. The invention also provides methods and media for use in the culture of biological cells, and particularly for the maintenance of undifferentiated biological cells in culture. The biological cells to be used therapeutically or to be cultured may preferably be stem cells or progenitor cells.

There are a growing number of contexts in which it is appreciated that biological cells may be utilised therapeutically. Perhaps the best known examples of therapies involving use of biological cells are:

i) gene therapy, in which biological cells are modified to express therapeutic gene products, and the modified cells administered to a subject requiring therapy;

ii) stem cell therapy, in which the multipotent properties of stem or progenitor cells are utilised to produce a therapeutic effect when the cells are administered to a subject requiring therapy (for instance by forming new tissue which may replace or augment damaged or abnormal tissues in the subject); and iii) immunotherapy, in which the immunological properties of biological cells are modified to produce a therapeutic effect, and the modified cells administered to a subject requiring therapy.

In each of the above examples the biological cells may be cells that are, or are derived from, cells isolated from the subject receiving therapy. In such cases the therapy is based on the use of autologous cells to achieve the therapeutic effect.

The advances in biological cell based therapies have created a need for techniques by which biological cells may be maintained ex vitro prior to their therapeutic use. The culture of stem or progenitor cells is particularly problematic using existing techniques. Current techniques make use of the activity of medium supplementation using serum, or cytokines such as interleukin-3 (IL-3), interleukin-11 (IL-11), stem cell factor (SCF) and Flt-3. ligand, to facilitate stem or progenitor cell propagation ex vivo. However, these existing techniques have many limitations, particularly in terms of their ability to maintain biological cells for sufficient time to allow their therapeutic adaptation, but without inducing cell maturation and differentiation. The ability to maintain stem or progenitor cells without causing maturation or differentiation of the cells is of great importance in maximising the effectiveness of therapies utilizing biological cells for a number of reasons.

Firstly, in the case of stem cell therapy, the therapeutic effect of the adapted cells relies on their multipotent nature, which allows the cells to generate replacement tissue in the subject receiving treatment. If cells to be used for therapy undergo uncontrolled differentiation during culture the number of possible lineages into which they may develop, and hence their ultimate therapeutic potential, is reduced.

Secondly, in other therapeutic contexts it may be desirable to induce the controlled differentiation of biological cells into a required cell type prior to their administration to a subject requiring therapy. Such controlled differentiation allows the cells to be manipulated to produce a desired cell type having the greatest therapeutic value and aids the subsequent targeting of the adapted cells to tissues requiring the therapeutic activity. Existing techniques, in which differentiation occurs not at the direction of the practitioner but rather under the uncontrolled action of the "cocktail" of cytokines present in serum or cytokine supplemented media, prevent the purposeful generation of desired cell lineages and may lead to the production of mixed cell populations thereby reducing therapeutic effectiveness.

To date, none of the prior art techniques have been consistently successful enough to allow their widespread clinical use in biological cell-based therapies. There therefore remains a need to develop improved methods for preparing biological cells for therapeutic use, and improved methods of therapy utilizing biological cells.

Furthermore, it will also be appreciated in the light of the above that there exists a need to develop new or improved cell culture methods, conditions and media capable of promoting biological cell growth without maturation and/or differentiation. Such new or improved cell culture resources may be of use not only in the therapeutic adaptation of stem and/or progenitor cells, but also in the culture of biological cells (and particularly stem and/or progenitor cells) for research and/or development purposes. Although it is desirable to be able to culture such cells (for example to allow expansion of cell numbers without maturation or differentiation) there is a general lack of suitable resources available to the skilled person in the prior art.

According to a first aspect of the present invention there is provided a method of preparing a biological cell for therapeutic use, the method comprising the consecutive or concurrent steps of:

i) culturing the biological cell in the presence of NM23 protein; and ii) adapting the biological cell for therapeutic use.

According to a second aspect of the present invention there is provided a method of therapy, the method comprising the consecutive or concurrent steps of:

i) obtaining a biological cell;

ii) culturing the biological cell in the presence of NM23 protein; and iii) adapting the biological cell for therapeutic use and further comprising administering the adapted biological cell to a subject in need of such therapy.

The NM23 gene family comprises eight human members, designated NM23-H1 to NM23-H8, which encode eight different isoforms of NM23 protein. It has been reported that NM23-H1 protein and NM23-H2 protein share 88% homology, and that NM23-H3 protein has 70% homology with the NM23-H1 and NM23-H2 proteins. There are also known homologues among other mammalian species, such as NM23-M1 the mammalian homologue of NM23-H1. The present invention relates to the use of NM23 proteins generally, but preferably to the use of human NM23 proteins, and most preferably to the use of the NM23-H1 protein.

The amino acid sequence of NM23-H1 protein is shown as Sequence ID No. 1, and the sequence of cDNA encoding the protein is shown as Sequence ID No. 2. NM23 proteins suitable for use in accordance with the various aspects of the invention may share at least 60% homology with the sequence of Sequence ID No. 1, and may preferably share at least 70% homology. More preferably NM23 proteins in accordance with the invention may share at least 80% homology with Sequence ID No. 1, even more preferably at least 90% homology, and most preferably at least 95% homology. Although it is preferred to use NM23 proteins with homology to NM23-H1, it will be appreciated that one of the most important factors in selecting a suitable agent for use in accordance with the invention is the degree of sequence identity shared with NM-23. Thus a suitable agent may share at least 60% identity with the amino acid sequence of Sequence ID No. 1, although preferred agents may share at least 70% identity, more preferably 80% sequence identity, even more preferably at least 90% sequence identity, and most preferably at least 95% sequence identity.

It will be appreciated from the preceding paragraph that the present invention relates not only to wild-type isoforms of NM23 protein, but also to mutant forms, fragments, derivatives and analogues of such proteins that are able to exert the same biological effect as wild-type isoforms. Such mutant proteins, fragments derivatives and analogues may be derived from NM23 proteins of any species, but are preferably derived from mammalian NM23 proteins, more preferably from human NM23 proteins, and most preferably from NM23-H1. Mutant proteins, protein fragments, derivatives and analogues suitable for use according to the invention may preferably be more biologically active, and/or more resistant to degradation, than wild-type proteins. Thus mutant proteins, protein fragments, protein derivatives and analogues may preferably have greater bioavailability to cultured cells, and indeed may have prolonged half-lives in culture conditions.

The inventors have surprisingly found that the beneficial effects of NM23 that make it suitable for use in accordance with the various aspects of the present invention are also able to be exerted across species barriers. Particularly, the inventors have found that human NM23 proteins (such as recombinant human NM23-H1) are able to produce advantageous biological effects in cultures of murine cells. The skilled person will immediately appreciate that this surprising finding indicates that the uses, methods and cell culture media of the invention are, even when employing human NM23 proteins, suitable for use in applications (other than therapeutic applications) in which non-human cells are grown: By way of example, culture of rodent cells represents a staple tool used in a range of research and development applications, and it will be appreciated that such cultures may benefit from the use of NM23 proteins derived from human and other non-rodent species. Equally, cultures of human cells may also benefit from supplementation with NM23 proteins derived from non-human sources.

The present invention is based upon the inventors' discovery that NM23 proteins are able to function as both survival factors for cultured cells, and also as agents capable of preventing cell differentiation and maturation. Accordingly, in a third aspect of the invention there is provided the use of NM23 protein to maintain undifferentiated biological cells in culture.

In a further aspect the present invention also provides the use of NM23 protein as a survival factor, and in a still further aspect there is provided the use of NM23 protein for the prevention of differentiation and maturation of cultured biological cells.

In view of their activity as survival factors and ability to prevent cell differentiation and maturation, the skilled person will appreciate that NM23 proteins are of great benefit in culture of cells that are to be adapted for use in therapeutic applications, since cells cultured in the presence of NM23 retain the greatest possible therapeutic effectiveness. NM23 proteins are also of use in the culture of biological cells for non-therapeutic purposes, since the same biological actions of these proteins also have utility in cell culture undertaken for a wide range of non-therapeutic purposes, including (but not limited to) research and development uses.

The inventors have found that NM23 proteins are able to exert their beneficial effects on cells that have been subject to cryopreservation, and the recognition of this benefit provides many advantages. For example, it is known that the process of freezing and thawing cells for cryopreservation is associated with a certain degree of cell death among the cells so preserved. This cell loss may have particularly adverse consequences in the case of small cell population subject to cryopreservation, in that the number of cells lost may often represent a relatively larger proportion of the total number of cells present. Typical examples of such small cell populations may include clinical or other therapeutic samples in which only relatively small numbers of cells may be obtained by available harvest protocols.

The skilled person will also appreciate that cryopreservation represents a routine technique used in the storage and/or transportation of stem and/or precursor cells whether destined for therapeutic or non-therapeutic applications, and that the applicability of the various aspects of the invention to "archival" cryopreserved stocks (i.e. existing stocks of therapeutic or non-therapeutic cells) is also particularly advantageous.

Conventional prior art techniques rely on the use of "cocktails" of multiple cytokines to promote stem or progenitor cell expansion ex vivo. The cytokines are typically provided either as part of, or in addition to, serum supplementation. Commercially available media intended for use in the expansion of stem cell populations include factors such as interleukin-3 and interleukin-11 (IL-3 and IL-11), stem cell factor and Flt-3 ligand. The presence of such cytokines, while helping to promote cell division, causes maturation and differentiation of the cultured cells. This maturation is outside the control of the practitioner, and represents a major disadvantage, since it decreases the number of different cell lineages to which the cells may ultimately give rise and may prevent controlled differentiation of the cells into preferred cell types.

In contrast to prior art techniques, the inventors have found that supplementation of cell culture medium with NM23 protein promotes cell survival without differentiation, and without the need to provide serum or exogenous growth factors. Multipotent cells cultured in the presence of NM23 protein and adapted for therapeutic use are particularly beneficial in therapy since they retain their capability to give rise to a wide range of cell types (i.e. retain their multipotent characteristics). In accordance with this finding it will be appreciated that in a preferred embodiment of the invention the cells are cultured in the presence of NM23 protein and media that are devoid of other cytokines or serum. In such use of NM23 protein in serum or cytokine free conditions the major function of NM23 may be to provide a survival signal for the cultured cells.

In a further aspect of the invention there is provided a culture medium supplemented with NM23 protein for the promotion of cell survival in culture without differentiation. The invention also encompasses NM23 protein formulated for use as supplement for a culture medium. The culture medium may preferably be a serum-free culture medium and/or a cytokine-free culture medium.

In an alternative preferred embodiment of the invention NM23 supplementation may be used in combination with other cell culture supplements such as serum, or cytokines (which may, for example, include such agents as interleukin-3, interleukin-6, thrombopoietin, Flt-3 ligand and/or stem cell factor). In such an embodiment the inventors believe that NM23 protein may serve to enhance the cultured cells' proliferation in response to the activity of the supplementing cytokines (i.e. NM23 may be used to augment proliferation in response to known cytokine supplementation regimes). Thus the supplementing cytokines may be selected for the ability to provide a proliferation stimulus that may otherwise be lacking from cells cultured in the presence of NM23 protein. The inventors also believe that the NM23 protein may act to prevent differentiation of the cultured cells that may otherwise take place in response to signals from supplementing cytokines (i.e. that culture conditions supplemented with NM23 protein may serve to promote cell proliferation while inhibiting the differentiation and/or maturation signals provided by known cytokine supplementation regimes).

In keeping with the modes of action described above, the inventors have found that NM23 supplementation allows stem cells populations to be expanded in culture using simpler cytokine cocktails than have previously been utilised (for example, expansion may be achieved in the presence of interleukin-3 and stem cell factor alone). Such relatively simpler cytokine cocktails may be expected to provide reduced differentiation stimuli to cells so cultured. Furthermore, the inventors have found that supplementation with NM23 protein increases the number of "self-renewal" divisions taking place in populations of stem and/or progenitor cells. These self-renewal divisions, in which dividing cells give rise to daughter cells where one daughter retains the same maturation status as the parent cell, constitute a defining characteristic of stem cell activity and populations, and the ability to increase the number of such divisions taking place is advantageous in terms of maintaining and/or expanding stem and/or progenitor cell numbers in cultured cell populations.

The inventors have found that the beneficial effects of NM23 supplementation may be achieved through continuous exposure to the NM23 protein until the desired biological outcome (e.g. cell population expansion or other advantageous effects herein considered) has been achieved. Alternatively the beneficial effects may also be achieved through early exposure of stem and/or progenitor cells to NM23, for instance during the first one, two, five, ten or fifteen days of culture, before subsequent withdrawal of NM23 supplementation.

It is preferred that the NM23 protein may be provided as an extracellular protein, for instance as a supplement to cell (or tissue) culture media. The NM23 protein provided may be an exogenous or recombinant protein. If the NM23 protein is to be provided in cell culture medium it may preferably be provided at between 0.01 µg/ml and 1 mg/ml, more preferably at between 0.25 µg/ml and 500 µg/ml, even more preferably at between 0.5 µg/ml and 50 µg/ml, and most preferably at between 0.5 µg/ml and 5 µg/ml.

Suitably NM23 protein for provision as an extracellular protein to cultured cells may be produced by known techniques. For instance, the protein may be purified from naturally occurring sources of NM23 protein. Indeed, such naturally occurring sources of NM23 protein may be induced to express increased levels of the protein, which may then be purified using well-known conventional techniques. Alternatively cells that do not naturally express NM23 proteins may be induced to express such proteins. One suitable technique involves cellular expression of an NM23 protein/his construct. The expressed construct may subsequently be highly purified by virtue of the his "tag".

Alternatively, cells cultured in accordance with the invention may be induced to over-express NM23 protein. This effect may be achieved either by manipulating endogenous NM23 protein expression, or causing the cultured cells to express exogenous NM23 protein. Expression of exogenous NM23 protein may be induced by transformation of cells with well-known vectors into which cDNA encoding NM23 proteins may be inserted. It may be preferred that exogenous NM23 protein is expressed transiently by the cultured cell (for instance such that expression occurs only during ex vivo culture and ceases on administration of the cells to the subject requiring therapy).

It will be appreciated that the gene encoding the NM23 protein may be delivered to the biological cell without the gene being incorporated in a vector. For instance, the NM23 gene may be incorporated within a liposome or virus particle. Alternatively the "naked" DNA molecule may be inserted into the biological cell by a suitable means e.g. direct endocytotic uptake.

The exogenous NM23 gene (contained within a vector or otherwise) may be transferred to the biological cells by transfection, infection, microinjection, cell fusion, protoplast fusion or ballistic bombardment. For example, transfer may be by ballistic transfection with coated gold particles, liposomes containing the exogenous gene, and means of providing direct DNA uptake (e.g. endocytosis).

The methods of the present invention are suitable for use with a wide range of biological cell types, but are preferably to be used with stem or progenitor cells. For the purposes of the present invention stem cells are taken to comprise totipotent or pluripotent cells, and progenitor cells (or precursor cells) to comprise multipotent cells. Totipotent cells are those cells capable of giving rise to any type of differentiated cell found in an organism, whereas pluripotent cells are those cells capable of differentiating into several different final differentiated cell types. Multipotent cells are cells able to give rise to diverse cell types in response to appropriate environmental cues (such as action of soluble growth factors or the substrate on which the cell, or its progeny, is located).

The methods of the invention may utilise mesenchymal stem or progenitor cells. Such cells are capable of giving rise to fat cells, bone cells or cartilage cells, and may be harvested from blood, bone marrow, the spleen or adipose tissue according to techniques known to the art.

It will be appreciated that the precise nature of the biological cell selected for use in accordance with the invention may be determined on the basis of the therapeutic use to which the cell is to be put. For example, in the case where it is desired to effect therapy of the haematopoietic system it may be preferred to utilise a biological cell derived from the haematopoietic system. Similarly, where it is wished to effect therapy of the central nervous system (CNS) it will be preferred to utilise a biological cell derived from the CNS, and where it is wished to effect therapy of the epidermis it will be preferred to use an epidermal cell. Equally, when cell cultures are to be used for non-therapeutic purposes the cells selected may be chosen with reference to the ultimate aim to be achieved. Thus in research and development applications of cell culture the cells to be cultured will generally be selected based on the research or development aim being investigated. Suitable protocols for the harvesting of biological cells for use in accordance with either the therapeutic or non-therapeutic applications of the invention will vary according to the source of the cells to be used. Cell harvest protocols are well known, and preferred protocols may be readily determined by those skilled in the art.

Preferably cells for use in the methods of the invention are collected from blood or bone marrow, most preferably from the peripheral blood. A most preferred method for collection of biological cells for use in accordance with the invention is described under 1.1 in the Example below.

Preferred culture conditions for use in accordance with the methods of the present invention may be determined with reference to the type of biological cell to be cultured. Consideration should be given both to the nature of the cell (e.g. stem or progenitor cell), to the source of the cell, and also to the manner in which the cell is to be adapted (in the case of therapeutic applications in accordance with the invention). Suitable culture conditions are well known to those skilled in the art. Indeed it is a particularly advantageous feature of the invention that existing cell culture techniques may be readily modified for use in accordance with the first and second aspects of the invention by the incorporation of NM23 protein and exclusion of other supplementary cytokines or serum.

By way of example, it may be preferred to culture blood-derived cells in RPMI 1640 medium supplemented with NM23 protein, or to culture mesenchymal cells in NM23 protein-supplemented DMEM medium (media readily commercially available from supplier such as Gibco BRL). The inventors have found that it is particularly preferred to culture cells in accordance with the protocol provided at 1.2 in the Example below.

Culturing cells in accordance with the present invention (e.g. step i) of the first aspect of the invention, or step ii) of the second aspect of the invention), may also involve ex vivo expansion of biological cell numbers. Such expansion may occur before, during, or after adaptation of the biological cells. The inclusion of NM23 protein (which the inventors have found acts as a survival factor for cultured cells) is particularly useful when expanding cell numbers in vitro.

Preferably culture in accordance with the invention, may also comprise isolation of the biological cell from a human or non-human donor. Preferably the donor may be the subject requiring therapy.

It will be appreciated that cells formed according to the method of the first aspect of the invention may be utilised in the diagnosis of disorders in utero, and that methods according to both the first and second aspects of the invention may be used in the correction of such disorders.

The methods of the first and second aspects of the invention may be particularly useful in providing biological cells that have been adapted to express enzymes having therapeutic activity. Such cells may be used to replace or augment damaged, missing or abnormal cells of the subject.

There are many different ways in which biological cells may be adapted for therapeutic use in accordance with the invention. The nature of the adaptation to be made will be determined by the therapeutic use to which the adapted cell is to be put.

Typical adaptations that may be made to biological cells in accordance with the invention to enable their therapeutic use include:
  i) adaptations for use in gene therapy;
  ii) adaptations for use in stem cell therapy; and
  iii) adaptations for use in immunotherapy.

Examples of adaptations of biological cells for therapeutic use, in accordance with the invention, are considered in greater detail below. The following pages consider the use of biological cells that have been therapeutically adapted in accordance with the methods of the invention for the treatment or prevention of a number of diseases and disorders. Except for where the context requires otherwise, it will be appreciated that the treatment or prevention of these diseases and disorders may be achieved using all embodiments of the second aspect of the invention, and is not limited to the specific adaptations considered below.

i) Adaptations for Use in Gene Therapy.

Gene therapy is a technology by which genes or small DNA or RNA molecules may be transferred to cells, either to correct existing genetic defects or to prevent or treat genetically linked diseases. Such therapies represent a potentially very powerful method by which a wide range of medical disorders may be treated. The term "gene therapy" encompasses a number of different techniques able to achieve therapeutic effects in a number of ways, but in its broadest form may be thought of as the use of any recombinant genetic material (such as DNA, RNA or hybrid molecules) transferred to biological cells to achieve a therapeutic effect.

The present invention is particularly applicable to "ex vivo" gene therapy, in which gene transfer is carried out in culture and the adapted cells then administered to a subject requiring therapy. Ex vivo gene therapy is highly effective, allowing tight control of the manipulation of the cell as well as permanent integration of therapeutic genes into the adapted cells.

The use of an ex vivo gene therapy approach has a number of advantages over the use of in vivo gene transfer (in which a vector is injected directly into a patient to be treated). One of the clearest advantages of such an approach is the ability to perform extensive safety controls before the insertion of cells into the patient being treated. In addition higher levels of therapeutic gene expression may potentially be produced, as cells may be selected for production of high levels of therapeutic protein prior to their injection into the patient. The advantages of ex vivo gene therapy largely arise as a result of the potential for further therapeutic manipulation and testing that is afforded by the maintenance, and possible expansion, in culture of the therapeutically adapted cells. Unfortunately the application of ex vivo gene therapy has until now been limited by the lack of suitable culture techniques allowing growth and manipulation of the adapted cells.

Gene therapy may be designed to block the effect of deleterious faulty genes, such as those involved in Huntington's disease, by use of so called short, interfering RNAs (siRNAs). Gene therapy may also be used to repair errors in messenger RNA derived from defective genes, and it is believed that this technique may have potential to treat various forms of cancer (including melanoma, leukaemia/lymphoma, prostate, ovarian and lung cancers) as well as other diseases such as cystic fibrosis and thalassaemia. Gene therapy has already been used in treatment of children with severe combined immunodeficiency disease, and it has been suggested that gene therapy may be useful in the treatment of neurodegenerative disorders such as Parkinson's disease. Other disorders that may be treated using gene therapy include haemophilia, familial hypercholesterolemia, Duchenne muscular dystrophy, AIDS and cardiovascular disorders.

Gene therapy also allows the development of DNA vaccines (which may be useful in the treatment of diseases such as malaria and AIDS, as well as endemic cancers such as Burkitt's lymphoma), and the production of replacement tissues and organs (expressing therapeutic genes) that may be used for transplantation.

Adaptation of a biological cell to make it suitable for gene therapy in accordance with the invention may typically comprise transformation of the cell to express a therapeutic product, typically a therapeutic gene product. Many suitable methods of adapting biological cells (such as stem cells and progenitor cells) in this manner are known to those skilled in the art. Typically cells may be transfected with a nucleic acid (herein referred to as a "therapeutic gene") that encodes a therapeutic product.

The therapeutic gene must be cable of being expressed by the adapted biological cells (preferably in vitro as well as when administered to a subject) yielding a product that, either directly or indirectly, has therapeutic activity. By "directly" we mean that the product of gene expression per se has therapeutic activity (for example a protein that replaces or augments abnormal protein expression in the subject). By "indirectly" we mean that the product of the therapeutic gene expression undergoes or mediates (e.g. as an enzyme) at least one further reaction to provide an agent having a therapeutic effect.

The therapeutic gene may be contained within a suitable vector to form a recombinant vector. The vector may for example be a plasmid, cosmid or phage. Such recombinant vectors are highly useful for transforming cells with exogenous genes.

Recombinant vectors may also include other functional elements. For instance, recombinant vectors may be designed such that the vector will autonomously replicate in the nucleus of the cell. In this case, elements that induce DNA replication may be required in the recombinant vector. Alternatively the recombinant vector may be designed such that the vector and recombinant DNA molecule integrates into the genome of a cell. In this case DNA sequences that favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The therapeutic gene, or genes, may be inserted into a retroviral vector. Such vectors may advantageously fully integrate into the host genome. This results in long-term gene expression, with integrated genes passed onto daughter cells.

It is preferred that the therapeutic gene is inserted in an adenoviral vector. The use of adenoviral vectors avoids the risk of insertional mutagenesis as the vector remains episomic and is not integrated into the genome. In addition the adenoviral vector has good transduction ability in quiescent, non-dividing, highly differentiated cells, a property that may prove useful if it is desired to induce differentiation of the adapted cells prior to their administration to the subject.

It will be appreciated that the therapeutic gene, or genes, may be delivered to the biological cell without the gene being incorporated in a vector. For instance, the therapeutic gene, or genes, may be incorporated within a liposome or virus particle. Alternatively the "naked" DNA molecule may be inserted into the biological cell by a suitable means e.g. direct endocytotic uptake.

The therapeutic gene, or genes, (contained within a vector or otherwise) may be transferred to the biological cells by transfection, infection, microinjection, cell fusion, protoplast fusion or ballistic bombardment. For example, transfer may be by ballistic transfection with coated gold particles, liposomes containing the exogenous gene, and means of providing direct DNA uptake (e.g. endocytosis).

It may be preferred that cells cultured in accordance with the methods of the invention and adapted for use in gene therapy may be induced to differentiate and adopt a desirable cell lineage or phenotype prior to their administration to a patient. Such differentiation may be of benefit in ensuring correct targeting of the adapted cells within the patient (i.e. to ensure that the cells take up residence in a preferred tissue compartment to be treated). Cells that are to be induced to differentiate in accordance with this embodiment of the invention may be transformed with the therapeutic gene, or genes, before or after differentiation has taken place. Suitable factors to induce the required differentiation will be well known to those skilled in the art, and may be determined with reference to the lineage or phenotype that it is desired for the cells to adopt.

ii) Adaptations for Use in Stem Cell Therapy.

Stem cell therapy represents a therapeutic method by which degenerative diseases (such as those caused by premature death or malfunction of cell types that the body is unable to replace) may be treated. It is hoped that addition of stem cells may help nucleate and promote the development of functional cells and/or tissues to replace those lost, thereby restoring normal healthy activity. Ultimately it may be possible to regenerate new functional tissues ex vivo which may then be administered to subjects requiring therapy.

The adaptation of biological cells for use in stem cell therapy may typically involve ex vivo expansion of stem cell or progenitor cell numbers in order to produce an increased stem cell population, the cells of which are suitable for administration to a subject requiring such therapy. In order to have therapeutic effectiveness, cells to be used in stem cell therapy (which may either be true stem cells or certain types of progenitor cells) must retain their ability to differentiate into multiple cell lineages when administered to a subject. Currently the application of stem cell therapy is limited by the lack of suitable methods by which stem cells may be propagated without undergoing differentiation and maturation.

Cells cultured in the presence of NM23 proteins are useful in methods of stem cell therapy since they promote stem cell survival in culture, and hence aid the expansion of stem cell numbers, but do not induce differentiation of the cultured cells.

It is believed that stem cell therapy may have wide applications across a broad range of diseases. For example stem cell therapy may be used in the treatment of blood disorders (such as leukaemia and sickle-cell anaemia), diseases of the brain and nervous systems (such as Parkinson's disease and Alzheimer's disease), musculo-skeletal disorders (such as muscular dystrophy, arthritis and osteoporosis), liver diseases (such as cirrhosis and hepatitis), spinal injuries, heart disease and diabetes.

Stem cell therapy may also be used to replace damaged tissue lost as a result of injury, trauma or cytotoxic insult. For example, such therapies may be used in neurodegenerative conditions, where CNS-derived stem cells may be utilised to replace or augment damaged somatic cells, such as those located in the brain or spinal cord. Stem cells may be used therapeutically in contexts in which the circulatory system has been injured, such as ischemic tissue damage after vascular occlusion. In such contexts suitable stems cells may be administered to cause formation of new blood vessels, or to replace other damaged tissues. Expanded populations of stem cells may also be utilised in conditions in which the liver has been damaged, in order to induce regeneration of the injured tissue.

iii) Adaptations for Use in Immunotherapy.

Immunotherapy relates to a wide range of therapeutic methods in which immunological properties of biological cells are manipulated such that the cells exert a therapeutic effect when administered to a subject requiring therapy. Thus immunotherapy-based adaptations in accordance with the present invention comprise any adaptation of biological cells that render the cells suitable for use in immunotherapy-based methods.

Stem and progenitor cells culture in the presence of NM23 proteins may be adapted such that their immunological properties are manipulated while maintaining the multipotent character of such cells. For example such a manipulation may include the ex vivo adaptation of cells to take on the properties of antigen presenting cells (APCs). Cells having APC characteristics may then be further manipulated in order to express antigens associated with microbes or cells that it is desired to eliminate from the subject. For example, biological cells may be manipulated ex vivo to present antigens characteristic of cancer cells. Upon administration of the adapted cells to a subject these adapted cells (having APC characteristics) are able activate T cells thereby inducing the subject's adaptive immune response to target and kill cancer cells present.

A method of therapy according to the second aspect of the invention may utilise biological cells that have undergone such immunotherapy-based adaptations as a monotherapy in the treatment of cancer (i.e. use of the biological cell-based therapy alone) or may be used in combination with, or as an adjunct to, other cancer therapies known in the art.

Administration of therapeutically adapted cells in accordance with the second aspect of the invention may typically be by introduction of the cells into the subject's body. Such administration may preferably be achieved by means of injection, implantation or inhalation. Preferred routes of administration may be readily determined with reference to the disease to be treated.

It will be appreciated that biological cells prepared and adapted in accordance with the invention are also suitable for use in the preparation and manufacture of medicaments. Therefore according to a further aspect of the invention there is a provided the use of a biological cell, cultured in the presence of NM 23 protein and adapted for therapeutic use, as a medicament. Medicaments in accordance with this aspect of the invention are suitable for use in the treatment of the diseases, disorders and injuries considered above.

Medicaments in accordance with the invention may be formulated according to protocols well known in the art. Suitable formulations may be determined based on the preferred route by which the medicament is to be administered. Preferably medicaments according to the invention may be prepared in forms suitable for administration by inhalation, by injection, or by implantation.

Preferably formulations for inhalation may preferably comprise biological cells provided in a suitable liquid carrier. Such a liquid carrier is preferably non-immunogenic, and may comprise a saline solution, cell culture medium, or distilled water. Formulations for injection may be as described above, or may also be provided in the form of a gel, which may preferably be capable of resolution by the body of the subject treated. Formulations suitable for implantation may take the forms described for injection or inhalation, and may also comprise biological cells provided in a scaffold or matrix capable of providing a foundation for new tissue development.

In both methods of therapy according to the second aspect of the invention, and in the use of medicaments according to the invention, a therapeutically effective amount of biological cells adapted for therapeutic use should be administered to the subject requiring therapy. A "therapeutically effective amount" is any amount of therapeutically adapted cells which, when administered to a subject suffering from a disease against which the therapeutically adapted cells are effective, causes reduction, remission, or regression of the disease. A "subject" may be a human being, or any other animal, particularly a domestic or agricultural mammal.

Figure 3:
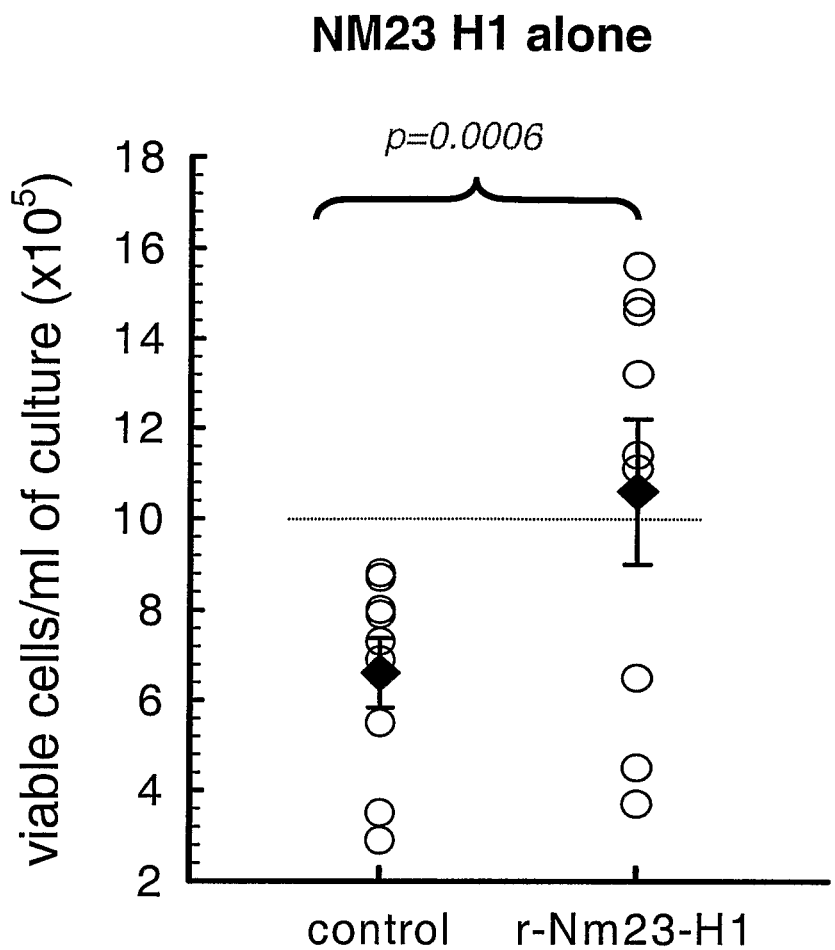
Figure 4:
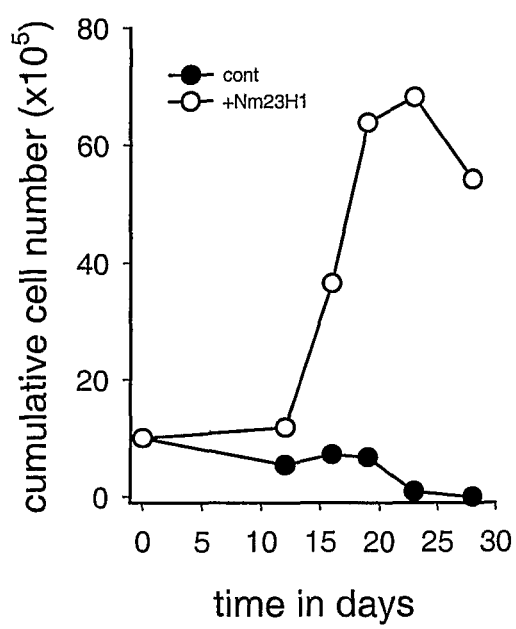
Figure 5:
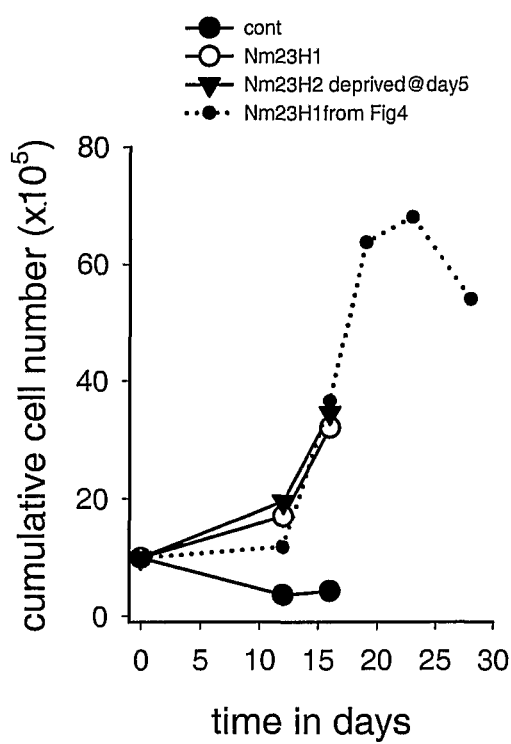
Figure 6:
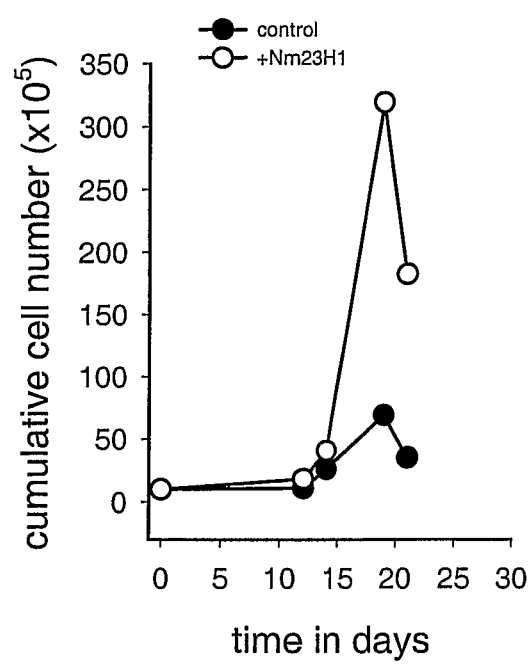
Figure 7:
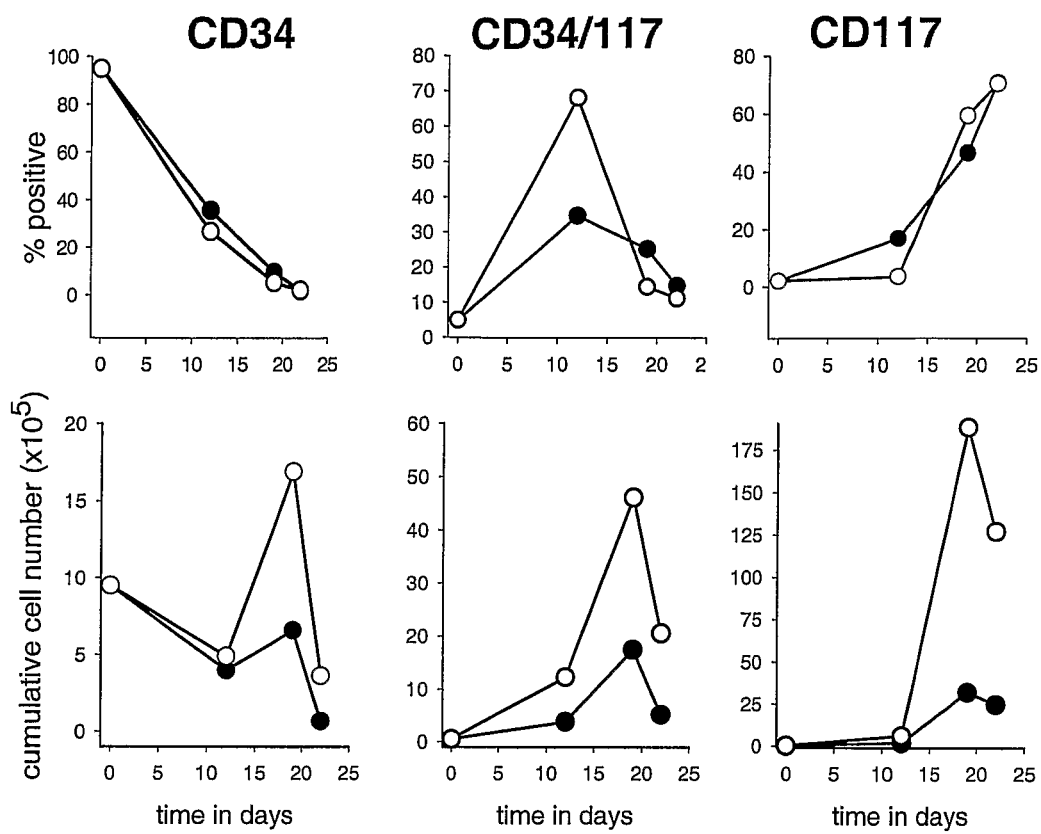
Figure 8:
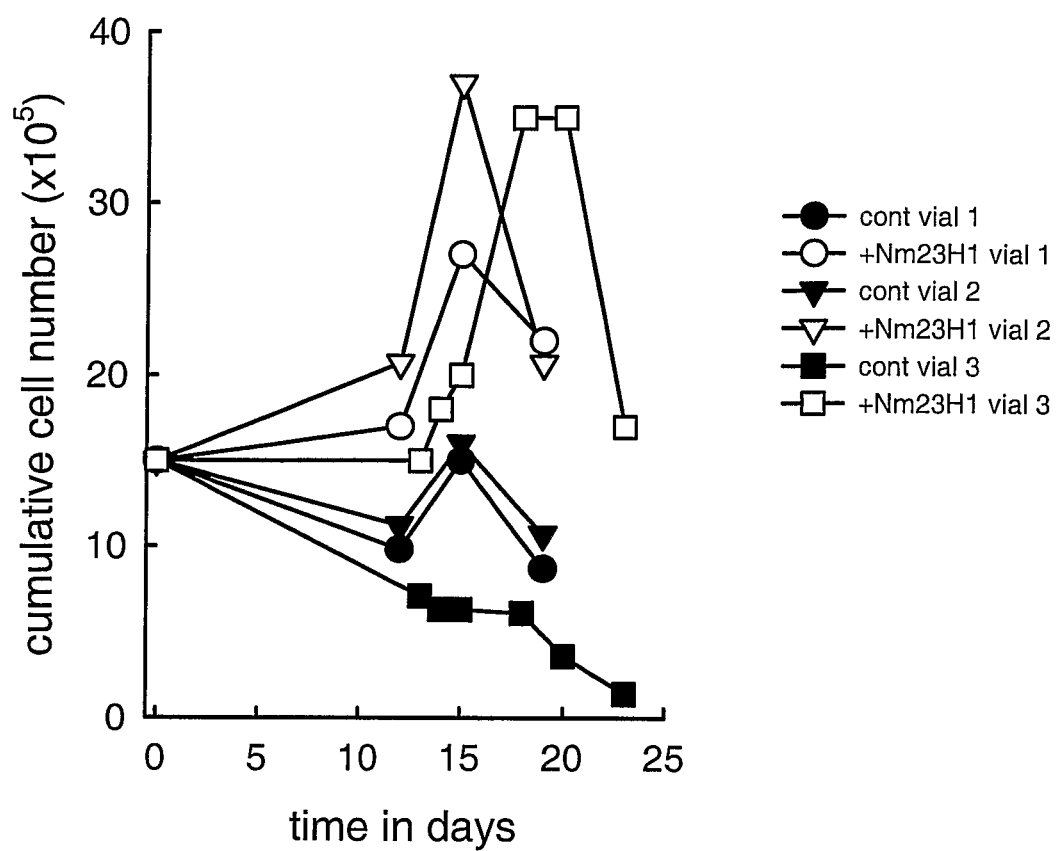
Figure 9:
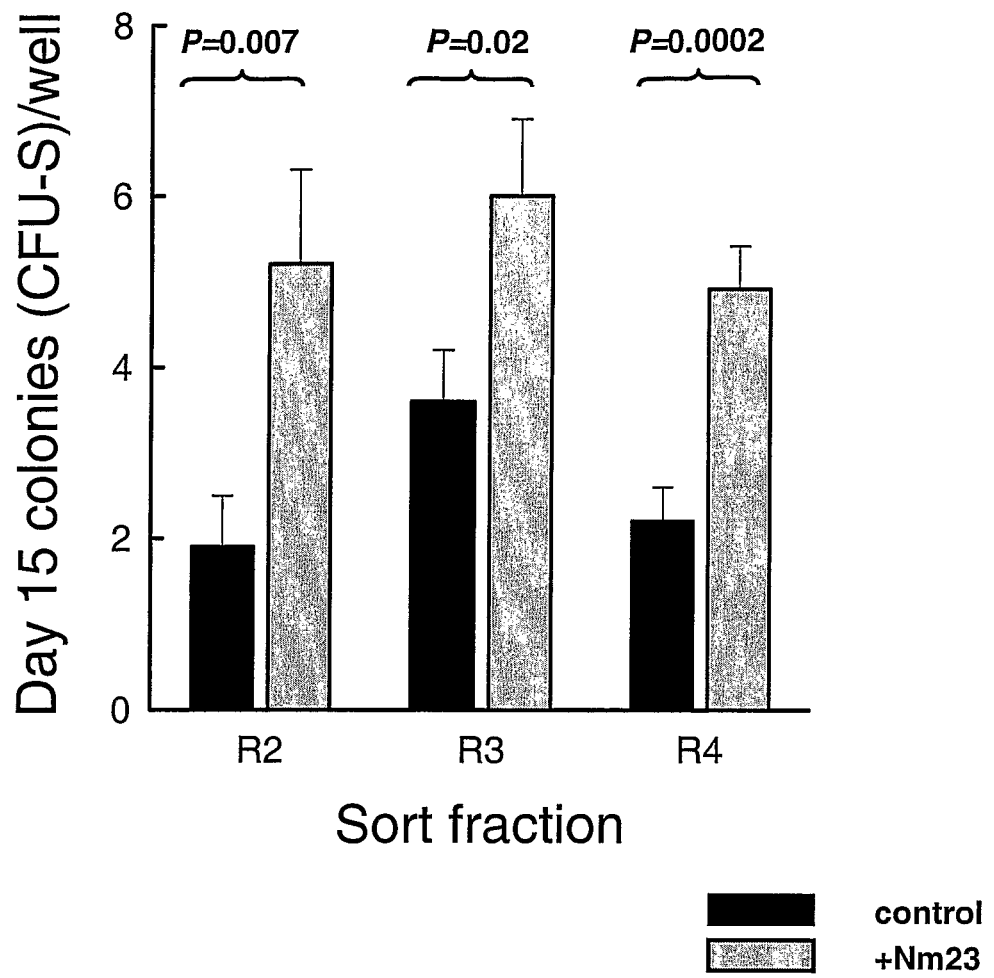

The invention will be illustrated further by the following Example, and with reference to the accompanying drawings, in which:

FIG. 1 relates to the identity of Nm23 H1. FIG. 1 provides the amino acid sequence of NM23 H1 (Sequence ID No.1) and Sequence ID No.2 provides the corresponding cDNA sequence used to encode expression of the protein defined in Sequence ID No.1;

FIG. 2 illustrates NM23 H1's function as a myeloid cell survival factor. The Figure shows the results of NM23 supplementation on the number of viable cells in cultures of primary AML cells obtained after ficol hypaque density centrifugation from the peripheral blood of a single AMNL patient. The AML cells were placed in culture at density of $10^6$ cells/ml in RPM 1640 medium containing ITS$^+$ and doses of recombinant human NM23 H1 as shown in the graphs. The results shown in the left hand panel are those obtained from cultures containing no additional cytokines (other than NM23) and those on in the right panel from cultures that were also treated with IL-3 and SCF. Cultures were harvested at day 5 and the numbers of remaining viable cells determined by phase contrast microscopy. The dashed line in the left panel shows the number of viable cells used to seed culture at day 0. All cultures that received NM23 H1 in conjunction with IL3 and SCF had cell numbers in excess of $10^6$ at day 5. P values were obtained using students T-test and are shown for the comparison of cultures containing 2 mg/ml to their respective no NM23 controls;

FIG. 3 illustrates that Nm23 H1 increases survival of cultured cells from multiple AML patients. AML cells prepared and cultured as described in the text and FIG. 2 were cultured in serum free medium in the absence and presence of 2 mg/ml rNm23 H1. After 5 days the cultures were harvested and the numbers of surviving cells determined as before. The data illustrated are for 9 consecutive AML samples (open circles) and their mean±s.e. P value was obtained using the paired t-test. The hatched line represents the numbers of cell used to seed the cultures at day 0. None of the cultures contained IL3 or SCF;

FIG. 4 shows that Nm23 H1 permits the expansion of cell numbers in cultures of CD34$^+$ cells from umbilical cord blood. CD34$^+$ cells were obtained from umbilical cord blood (UCB) as described in the Examples section. The resulting cells were cultured at $10^6$/ml in RPMI 1640 medium supplemented with ITS$^+$, IL3 and SCF and either in the presence or absence of rNM23 H1. Cultures were sampled at the times shown to allow enumeration of surviving cells. Cultures were fed as required to prevent overgrowth or exhaustion of the medium;

FIG. 5 illustrates that the effect of NM23 H1 is achieved through activity upon newly isolated cells and their progeny. UCB were isolated and cultured as for FIG. 4 above. Cells were either cultured without NM23 H1 (larger closed circles) or with NM23 supplementation. In some of the cultures investigated NM23 H1 supplementation was removed at day 5 (closed triangles) and in others NM23 H1 supplementation was sustained for the full term of the study (open circles). The data show that the proliferation of cells treated with the two different NM23 H1 supplementation regimes was identical. Interestingly, although these cultures were only maintained to day 16, over this time period the NM23 H1 treated cohorts behaved near identically to the cells from a separate donor originally shown in FIG. 4 and repeated here as the hatched line. These data may indicate that the action of NM23 is instructive to the cells and the information 'learned' is sustained post day 5 (i.e. that the biological effects of NM23 supplementation at early time points are continued even when the supplementation is subsequently removed). Alternatively the data may be taken to illustrate that the critical survival signal provided by NM23 H1 in the early days of the culture allows more cells to contribute to the subsequent expansion of the culture;

FIG. 6 shows that the effects of NM23 H1 supplementation are recapitulated in cultures of CD34$^+$ cells derived from mobilized adult peripheral blood. CD34$^+$ cells were positively selected from mobilized blood mononuclear cell preparations provided the Blood Transfusion Service stem cell laboratories in Birmingham. The resulting cells were cultured at $10^6$/ml in RPMI 1640 medium supplemented with ITS$^+$, IL3 and SCF and either in the presence or absence of rNM23 H1. Cultures were sampled at the times shown to allow enumeration of surviving cells. Cultures were fed as required to prevent overgrowth or exhaustion of the medium;

FIG. 7 allows analysis of early maturation events in cultures of CD34$^+$ cells derived from mobilized blood. Samples of cells were harvested at the times shown from the cultures described in FIG. 6 and analysed by dual fluorochrome cells sorting analyses using a Becton Dickenson FACS caliber machine. The left hand panels show the dynamics of CD34$^+$/CD117$^-$ cells in the cultures. The central panels and right hand panels show dynamics of CD34$^+$/CD117$^+$ and CD34$^-$/CD117$^+$ cells respectively. Upper panels show the data as percentage cells expressing the markers and the lower panels the absolute numbers of cells expressing the markers. The open circles represent data from cultures supplemented with NM23 H1 the closed circles cultures without NM23 H1 supplementation. It is worth noting that in the absence of NM23 H1 supplementation the numbers of CD34-single positive (i.e. CD34$^+$/CD117$^-$) fell more or less progressively, whereas the numbers of these cells were expanded between days 12 and 16 in cultures supplemented with NM23 protein;

FIG. 8 shows that supplementation with NM23 H1 protein promotes rescue of stored cryo-preserved CD34$^+$ cells. Cryogenically stored haemopoietic stem cells represent a source of cells widely expected to be useful in the management of a range of diseases. One example of such a use is that of syngeneic stem cell transplants administered post myeloablative treatment for leukaemia. The relatively low quality/recovery of cells post cyro-preservation presently constitutes a limitation to the success of existing prior art procedures. Data shown in the Figure are derived from three individual experiments in which CD34$^+$ cells have been purified from separate vials of a cryo-preserved mobilized peripheral blood mononuclear cell preparation. In all three cases cell survival of these cells was markedly enhanced by supplementation with NM23 H1 (open symbols); and FIG. 9 illustrates that supplementation with NM23 H1 also causes expansion of murine progenitor cell numbers in liquid culture. Established methodologies (J. Exp. Med. 183: 1797-1806 (1996)) were used to sort 'side population' (SP) mouse stem cells as three fractions from the bone marrow of normal mice and the cells cultured for five days in DMEM supplemented with horse serum and a cytokine cocktail designed to expand stem/progenitor cell numbers (SCF 20 ng/ml, TPO 25 ng/ml, IL3 10 ng/ml, IL6 10 ng/ml and Flt-3$_L$ 10 ng/ml). These cultures were established either in the absence or presence of NM23 H1. After 5 days the cells were transferred into long-term culture initiating cell (LTC-IC) assays in the absence of NM23 H1. In the assay used, primitive stem and/or progenitor cells pass underneath a pre-formed stromal culture whereas more mature cells stay above the stromal layer. When the primitive cells begin to proliferate they first do so under the stromal cells and only when they begin to mature do they traverse the stem cell layer. The proliferation of progenitor cells beneath the stromal layer creates formations with the appearance of "cobblestones". Scoring of these colonies allows an estimation of the numbers of stem/progenitor cells present in the cell population used to seed the LTC-IC assay. There is a time differential in the generation of cobblestone colonies with more primitive cells generating colonies after several days and more mature progenitors giving colonies much sooner. The data shown here are for colonies identified two weeks after establishing LTC-IC assays. Colonies detected at this time are considered to be derived from pluripotent haemopoietic stem/progenitor cells with similar reconstituting properties to positively sorted human CD34$^+$ cells. The data show that, in all three fractions of SP cells and despite the presence of a rich supportive cytokine mix, supplementation with NM23 protein whilst in liquid culture either resulted in greater preservation of repopulating cells or enhanced the expansion of such cells.

EXAMPLE 1

Protocols
1.1. Cell Harvesting.
AML blast cells were isolated from peripheral blood (provided after informed consent) using Ficoll Hypaque cell density centrifugation.
1.2. Cell Culture.
After harvesting, the cells were cultured overnight in RPMI 1640 medium supplemented with a commercial serum replacement (ITS$^+$) and containing human recombinant interleukin 3 (IL3) and stem cell factor (SCF) (both at 5 ng/ml).
The next day cells were washed twice (RPMI 1640; no ITS$^+$ nor cytokines) counted and adjusted to $1 \times 10^6$ cells/ml in RPMI 1640 supplemented with ITS$^+$ and with or without IL-3 and SCF. Cells were plated as 1 ml cultures (in 48 well plates) in the presence and absence of recombinant human Nm23 H1 (provided at concentrations up to a maximum of 2 µM).
After 5 days cells were harvested and the number of viable cells /ml of culture determined by the use of a haemocytometer and phase-contrast microscopy. Data showing dose responses to Nm23 H1 are for a single AML sample and the data points are the mean±SE of quadruplicate cultures. Data for the third figure are for n=9 consecutive AML samples received into the lab and that fitted the criteria of cells having high viability (>90%) after the initial overnight culture in the presence of IL-3 and SCF. These experiments used media without cytokines and the presence and absence of 2 µg/ml Nm 23 H1.
1.3. Expression and Purification of Recombinant NM23 H1.
cDNA encoding NM23 H1 was inserted into the pET15b plasmid (Novagen) which carries an N-terminal His tag.
The protein product of the plasmid (i.e. NM23 H1 with a N-terminal His tag) was expressed in *E. coli* BL-21 (DE3) strain. Expression was induced using isopropyl-beta-D-thiogalactopyranoside (IPTG) in accordance with standard protocols.
The recombinant protein was purified using a conventional Nickel ion-chelated NTA agarose system according to protocols provided (Ni-NTA His-Bind Kit, Novagen).
Results
1.4. Recombinant Nm23 H1 Acts as an Stem and Progenitor Cell Survival Factor and Does Not Cause Differentiation of Cultured Cells.
The inventors tested whether recombinant NM23 H1 protein, produced and purified according to the method set out in 1.3 above, was able to promote the survival of primary acute myeloid leukemia AML cells (which provide an experimental model for stem or progenitor cells) without inducing their differentiation.
FIG. 2 shows data obtained from single AML samples incubated for 5 days with increasing N23 H1 concentrations either in the absence of supporting cytokines (left panel) or in the presence of interleukin-3 (IL-3) and stem cell factor (SCF) (right panel).
Cultures were seeded at day 0 with $10 \times 10^5$ cells (dashed line). The data show that NM23 H1 improved cell survival in the absence of cytokines and improved overall proliferation in their presence. Furthermore the AML cells cultured in the absence of other cytokines did not undergo maturation or differentiation during the period for which they were cultured.

FIG. 3 shows collective data from n=9 AML samples cultured for five days in the presence or absence of 2 μg/ml Nm23 H1 (without supporting cytokines). The dashed line again defines the number of cells plated at day 0.

The data shown in FIG. 3 illustrate that all AML samples cultured in the absence of NM23 H1 (nine out of nine cultures tested) suffered loss of cells over the five day test period. In contrast two thirds of the samples cultured in the presence of NM23 H1 in (six out of nine cultures tested) did not suffer cell loss, and in these cultures cell numbers remained the same or increased.

Conclusions
1.5.

The results set out in this Example illustrate that, in an experimental model of stem or progenitor cell culture, populations of cells grown in the presence of NM23 protein (and without the addition of other cytokines) are able undergo expansion and are not subject to differentiation or maturation.

These results illustrate the effectiveness of NM23 protein in the propagation of biological cells that may, before, during or after such culture, be adapted for therapeutic use.

EXAMPLE 2

2.1 Experimental Design.

The following experiments were undertaken to investigate the activity of Nm23 H1 on human $CD34^+$ stem or progenitor cells. The experiments investigate the effects of NM23H1 on such cells derived from neonatal umbilical cord blood or mobilized peripheral blood.

The human stem or progenitor cell sources selected represent the only stem cell populations that are currently used in routine stem cell therapy. The stem cell therapy for with these cells are used takes the form of transplantation of stem cells to recipients that have undergone treatments such as myeloablative therapies (for example in the treatment of leukaemia). The transplanted stem cells are then able to reconstitute the haemopoietic system of the recipients. Most often stem cell transplantation of the type described above utilizes stem cells derived from mobilized peripheral blood. This procedure makes use of the fact that stem cells of patients treated with suitable cytokines, such as granulocyte colony stimulating factor (G-CSF), become 'mobilized' and vacate the bone marrow into the peripheral blood. As a result the mobilized stem cells may be relatively readily harvested from the circulation of the donor.

It is generally recognized that CD34 expression constitutes a useful marker for stem and precursor cells. In practicing the stem cell transplantation techniques described above $CD34^+$ cells are not usually sorted but their numbers within the mobilized fraction are nonetheless considered to be an accurate enumerator of the stem cell number present in the fraction. Recipients generally receive a variable number of total donor cells amongst which they receive a constant number of $CD34^+$ cells.

In some allogeneic transplant scenarios it is necessary to deplete T-lymphocytes from donor stem cell preparations in order to prevent (or at least limit) the risk of graft-versus-host disease. Selection of $CD34^+$ cells using techniques such as immunomagnetic separation allows a 3-4 log depletion of T-cells to be achieved, while preserving a high number of hematopoietic stem or progenitor cells in the cell population to be grafted (reviewed recently in Platzbecker U et. al: Leuk Lymphoma. March 2004; 45(3):447-53).

A second source of stem or progenitor cells capable of re-constituting the haemopoietic system of adults comprises umbilical cord blood (UCB) taken at time of birth. UCB contains a much greater number of circulating stem cells than does adult blood and these cells can be harvested from placenta post partum. As is the case with stem or progenitor cells collected from mobilized blood, sorted $CD34^+$ cells from UCB are able to act as re-populating stem cells.

The following experiments investigate the effects of NM23 proteins on immunomagnetically selected $CD34^+$ cells derived from both mobilized peripheral blood into which stem cells have been artificially mobilized, and also from UCB.

2.2 Protocols.

UCB was provided under Local Research Ethics Committee (LREC) approval and parental informed consent by the delivery suite at the Birmingham Womens Hospital (University Hospitals of Birmingham Trust). Informed consent to use excess mobilized blood was obtained prior to provision of the relevant donations.

Cord blood was diluted 1:3 using RPMI 1640 medium, and mononuclear cell preparations prepared by layering over Ficoll Hypaque and centrifugation. Harvested cells were washed twice with PBS containing 2% FBS (foetal bovine serum) prior to selection of $CD34^+$ cells. Mobilized blood was provided as a mononuclear preparation by the Blood Transfusion Service Stem Cell laboratories, Birmingham.

$CD34^+$ cells were sorted using magnetic cell separation columns (Miltenyi) using the manufacturers indirect selection kit and protocols. Sorted cells were placed in serum free RPMI 1640 medium supplemented with a commercially available serum replacement ($ITS^+$: Becton Dickenson) and containing rh-IL3 and rh-SCF (as used in earlier studies using AML cells).

In the case of mononuclear cells derived from mobilized blood, samples of cells were also stored in liquid nitrogen using standard protocols for the storage of viable cells and $CD34^+$ cells selected after thawing of the frozen cell stocks.

Directly sorted $CD34^+$ cells were plated at $1 \times 10^6$/ml, while sorted cells from thawed stocks were plated at $1.5 \times 10^6$/ml. Cultures were incubated at 37° C. in a humidified atmosphere containing 5% $CO_2$, either in the presence or absence of 2 μg/ml of rh-Nm23 H1.

2.3 Results.

Effect of NM23 Protein on Stem or Precursor Cells from Umbilical Cord Blood.

FIGS. 4 & 5 illustrate representative data generated from experiments using $CD34^+$ cells harvested from UCB.

2.3.1

FIG. 4 illustrates the results of an experiment in which $CD34^+$ cells were harvested and then cultured for 28 days. As illustrated in FIG. 4 cultures treated with NM23 H1 exhibited a marked expansion of cell numbers as compared to cultures that were not treated with Nm23 H1. By the sixteenth day of culture both NM23-treated and untreated cultures contained many $CD34^+$ cells, however the number of such cells in the NM23-treated cultures was much increased compared to that found in the untreated cultures.

2.3.2

FIG. 5 illustrates data from a separate experiment using $CD34^+$ cells derived from UCB in cultures maintained for a total of sixteen days. The data from the NM23 H1-treated group in experiment 2.3.1 are also included in FIG. 5 for illustrative purposes.

In this second experiment the purified CD34$^+$ cells were divided into three groups as follows:

a) cultures not provided NM23 H1 during the experiment (labeled "cont" in FIG. 5);
b) cultures supplemented with NM23 H1 for the duration of the experiment; and
c) cultures provided with NM23 H1 during the first five days of culture, the NM23 supplementation subsequently being removed at day five.

It can be seen from FIG. 5 that both groups b) and c) NM23 H1 exhibited the same population kinetics as the NM23 H1 treated cells from experiment 2.3.1. This finding illustrates that the removal of NM23 H1 from group c) at day five did not lead to reduced cell numbers compared with the effects observed in groups treated with NM23 throughout the experiment. These observations indicate that the cell-maintenance effects of NM23 H1 treatment are exerted on the CD34$^+$ stem or progenitor cell population, and not upon their differentiating progeny.

Effect of NM23 Protein on Mobilized Stem or Precursor Cells Isolated from Peripheral Blood.

2.3.3

FIG. 6 shows the effect of NM23 H1 on the expansion CD34$^+$ cells harvested from peripheral blood containing mobilized stem or progenitor cells. As shown the expansion in stem or progenitor cell numbers observed was similar to that obtained using stem or progenitor cells derived from UCB (comparison with the results of experiments 2.3.1 and 2.3.2). The data illustrate that supplementation with NM23 of stem or progenitor cells cultures derived from cells mobilized into the peripheral blood was able to achieve not only the maintenance of CD34$^+$ cells but also an expansion of their numbers (comparable expansion to the results shown in FIG. 7).

2.3.4

The early events during the commitment to differentiation of CD34$^+$ cells mobilized into the peripheral blood can be monitored by the gain of CD117 expression and subsequent loss of CD34 expression. Thus as the cells differentiate they follow a sequence of first being "CD34 single positive" (i.e. expressing CD34 but not CD117) before becoming "CD34/CD117 double positive" (i.e. expressing both CD34 and CD117) before finally becoming "CD177 single positive" (expressing CD117 but not CD34).

The upper panels of FIG. 7 illustrate data obtained by FACS-analyses of the cultures described in Experiment 2.3.3. (results of which are shown in FIG. 6). The results illustrated in FIG. 7 show the progressive fall in CD34-single positive cells, the transient expansion of CD34/CD117 double positives and the subsequent rise in CD117 single positives.

These data illustrate that in culture conditions supplemented with NM23 H1 some degree of cell maturation occurs, however when these results are considered in combination with the cell number data (illustrated in FIG. 6) and the percentage data (from the upper panels of FIG. 7) it is apparent that the total number of CD34 single positive cells present in NM23 supplemented cultures undergoes marked expansion, as shown in the lower panels of FIG. 7.

The data shown in the lower panels of FIG. 7 illustrates that in cultures supplemented with NM23 H1 the actual number of CD34-single positive cells (indicative of stem or precursor cells having the lowest degree of differentiation and maturation) is not only maintained, but is markedly expanded. For instance, it can be seen that after nineteen days in cell culture conditions those cultures supplemented with NM23 protein contained nearly twice as many CD34 single positives as were initially introduced into the culture (value for day zero illustrated in graphs).

These results thus provide a clear illustration of the fact that cell cultures supplemented with NM23 protein allow a significant expansion of the number of stem and/or precursor cells. These stem and/or precursor cells are maintained without differentiation and with number of non-matured stem and/or precursor cells present in the culture is significantly increased.

2.3.4

The suitability of NM23 H1 protein to bring about expansion of transplantable stem and/or precursor cells that have been subjected to cryo-preservation was also investigated. The inventors undertook NM23 supplemented cell culture of CD34$^+$ cells that had been immunomagnetically selected after thawing of cryo-preserved mobilized blood mononuclear cell samples. The results of this study are shown in FIG. 8.

FIG. 8 illustrates data from CD34$^+$ cells separately purified from three individually thawed mononuclear cell preparation vials derived from the same mobilized blood donation sample. In each case, and as observed in the previous experiments reported above, NM23 H1 supplementation of cell culture conditions resulted in the expansion of CD34$^+$ cell numbers beyond the initial number of stem or precursor cells initially inoculated into the cultures and to a far greater extent than was observed in parallel control cultures.

These results clearly illustrate that NM23 protein is able to exert its beneficial biological effects on stem and/or precursor cells that have been stored in cryopreserved conditions (conditions commonly used in the transport or archival storage of stem and/or precursor cells destined for clinical or research use). It will be readily appreciated that this finding further illustrates the advantages provided supplementation or treatment of cell cultures with NM23 since it shows that NM23 protein is able to expand stem and/or precursor cell numbers in pre-existing archival stem or precursor cell samples, and also to overcome the degree of cell loss normally associated with the "freezing" of stored cells (important in cases where only relatively small numbers of stem or precursor cells are obtained by harvest protocols).

Effect of Human NM23 Protein on Non-Human Cell Culture.

2.3.5

The inventors undertook preliminary investigations into the ability of human NM23 proteins to promote expansion and survival of stem and/or precursor cells derived from different mammalian species. These results indicate that the advantages of NM23 supplementation are broadly effective across species barriers, thus greatly increasing the range of contexts (particularly those involved with research and/or development) in which the present invention may be of benefit.

In a pilot experiment, the inventors have taken mouse 'side' population cells that represent very primitive haemopoietic stem cells and cultured these in liquid medium with a supportive cytokine cocktail (comprising SCF 20 ng/ml, thrombopoietin 25 ng/ml, IL-3 10 ng/ml, IL-6 10 ng/ml and Flt-3 Ligand 10 ng/ml) over a five day period either in the presence or absence of rh-NM23 H1.

The cultured cells obtained were then placed in long-term culture initiating cell (LTCIC) assays. In assays of this kind colonies of progenitor cells can be identified by their characteristic 'cobblestone' appearance that arises due to their proliferation below stromal cells used the LTCIC assay. Whence the precursor cells undergo commitment to terminal differentiation they then migrate through the stromal cell layer and differentiate above the stromal cells. Thus the number of cobblestones present provides a measure of the number of stem cell/progenitor cells being brought in to cell cycle but that have not yet undertaken terminal differentiation. New cobblestone areas arise over time, and the development of later-developing colonies reflects the presence of more primitive stem/progenitor cells in the population used to seed the LTCIC cultures.

The inventors initiated LTCIC cultures using three separately sorted side populations derived from a common donor mouse. The cultures were analyzed for the presence and number of cobblestone areas after fifteen days of cell culture conditions. The results of these experiments are shown in FIG. 9.

In each case a significantly higher number of cobblestone colonies arose from the NM23 H1 treated cells indicating that mouse haemopoietic progenitor/stem cells are also supported in liquid culture by the provision of NM23 H1. Although they do not wish to be bound by any hypothesis, the inventors believe that this effect may arise as a result of the fact that the protein sequences of NM23 H1 and its mouse homologue (NM23 M1) are highly conserved.

2.4 Discussion.

The experiments describe above illustrate that supplementation with NM23 proteins such as NM23-H1 has value in the arena of conventional and established stem cell therapies. The observation that CD34-single positive cells can be maintained and indeed their numbers increased in culture over a period of approximately three weeks further illustrates the applicability of the invention in the context of stem cell mediated gene therapies since the period in culture is comparable to that required by current protocols for genetic manipulation of cells in vitro.

In our culture system NM23 showed some ability to delay the maturation of the stem or precursor cell cultures as a whole and also, more noticeably, expanded the numbers of cells in each compartment. It is possible that combining NM23 supplementation with beneficial cytokine mixes (and particularly cytokine mixes other than those used in the experiments described above) may further delay maturation and thereby afford even greater expansion of stem cell numbers in response to NM23 treatment.

Apart from the potential clinical advantages provided by NM23 supplementation of stem or precursor cell populations destined for therapeutic manipulation and use, the data presented here illustrate that culture in the presence of NM23 may be of notable benefit in that context of stem and/or precursor cell culture for purposes of scientific research and development. A great deal of research is conducted worldwide into the biology of haemopoietic progenitors and stem cells, but until now this research had been limited by the lack of suitable cell culture conditions, protocols and media able to satisfactorily support stem and/or precursor cell expansion (particularly in the absence of cell differentiation and/or maturation). Supplementation with NM23 protein is able to overcome, or at least reduce these problems, and so it will be recognized that the capacity of NM23 proteins such as NM23 H1 to promote the survival of stem or precursor cells ex-vivo is of considerable value and scientific importance. The results set out above further illustrate that supplementation with NM23 is effective in the culture of cells derived from diverse mammalian species.

The invention claimed is:

1. A method of maintaining stem cells in culture in vitro comprising culturing the stem cells in the presence of NM23 protein, without any cytokines other than cytokines IL-3 and/or SCF, wherein the NM23 acts to inhibit differentiation and maturation of said cultured stem cells.

2. The method of claim 1, wherein the NM23 protein acts as a survival factor for said cultured stem cells.

3. The method of claim 1, wherein the cultured stem cells are for therapeutic use.

4. The method of claim 1, wherein the cultured stem cells are for non-therapeutic use.

5. The method of claim 1, wherein the cultured stem cells are selected from the group consisting of mesenchymal stem cells, haematopoietic stem cells, stem cells of the central nervous system (CNS) and epidermal stem cells.

6. The method of claim 1, wherein the stem cells are collected from the blood or bone marrow.

7. A cell culture medium for the promotion of stem cell survival in culture without differentiation, the culture medium comprising:

NM23 protein in an amount sufficient to inhibit differentiation and maturation of the stem cells in the culture; and an effective amount of cytokine selected from the group consisting of IL-3, SCF, and combinations thereof, and wherein the medium contains no other cytokines.

8. The cell culture medium according to claim 7, wherein the stem cell is selected from the group consisting of a mesenchymal stem cell, a haematopoietic stem cell, a stem cell of the central nervous system (CNS), and an epidermal stem cell.

9. The cell culture medium according to claim 7, wherein the stem cell is collected from blood or bone marrow.

10. The cell culture medium according to claim 7, wherein the stem cell culture medium comprises RPMI 1640 medium.

11. The cell culture medium according to claim 7, wherein the stem cell culture medium comprises DMEM medium.

12. A composition comprising the stem cell culture medium according to any of claims 7-11 in contact with said stem cell.

* * * * *

SEQUENCE LISTING

<160> NUMBER OF SEQ ID NOS: 2

<210> SEQ ID NO 1
<211> LENGTH: 152
<212> TYPE: PRT
<213> ORGANISM: homo sapiens

<400> SEQUENCE: 1

```
Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
        35                  40                  45

Lys Glu His Tyr Val Asp Leu Lys Asp Arg Pro Phe Phe Ala Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
        115                 120                 125

Glu Ile Gly Leu Trp Phe His Pro Glu Glu Leu Val Asp Tyr Thr Ser
    130                 135                 140

Cys Ala Gln Asn Trp Ile Tyr Glu
145                 150
```

```
<210> SEQ ID NO 2
<211> LENGTH: 459
<212> TYPE: DNA
<213> ORGANISM: Artificial sequence
<220> FEATURE:
<223> OTHER INFORMATION: cDNA for NM23 H1 protein

<400> SEQUENCE: 2
atggccaact gtgagcgtac cttcattgcg atcaaaccag atggggtcca gcggggtctt        60
gtgggagaga ttatcaagcg ttttgagcag aaaggattcc gccttgttgg tctgaaattc       120
atgcaagctt ccgaagatct tctcaaggaa cactacgttg acctgaagga ccgtccattc       180
tttgccggcc tggtgaaata catgcactca gggccggtag ttgccatggt ctgggagggg       240
ctgaatgtgg tgaagacggg ccgagtcatg ctcggggaga ccaaccctgc agactccaag       300
cctgggacca tccgtggaga cttctgcata caagttggca ggaacattat acatggcagt       360
gattctgtgg agagtgcaga gaaggagatc ggcttgtggt ttcaccctga ggaactggta       420
gattacacga gctgtgctca gaactggatc tatgaatga                              459
```